United States Patent [19]

Vollmer et al.

[11] Patent Number: 4,574,117
[45] Date of Patent: Mar. 4, 1986

[54] STABILIZATION OF PHENYLALANINE AMMONIA-LYASE IN A BIOREACTOR USING REDUCING AGENTS

[75] Inventors: Patricia J. Vollmer; Jeffrey J. Schruben, both of Paducah, Ky.

[73] Assignee: Genex Corporation, Rockville, Md.

[21] Appl. No.: 617,805

[22] Filed: Jun. 6, 1984

[51] Int. Cl.$^4$ .................. C12P 13/22; C12N 9/96; C12N 9/88

[52] U.S. Cl. ................... 435/108; 435/188; 435/232

[58] Field of Search .................. 435/108, 188, 232

[56] References Cited

U.S. PATENT DOCUMENTS 4,277,562  7/1981  Modrovich ..................... 435/17

FOREIGN PATENT DOCUMENTS 1489468  10/1977  United Kingdom .

OTHER PUBLICATIONS

Yamada, et al., Production of L-Phenylalanine from trans-Cinnamic Acid with Rhodotorula Glutinis Containing L-Phenylalanine Ammonia-Lyase Activity, Applied and Environmental Microbiology, Nov. 1981, pp. 773-778, vol. 42, No. 5.

Primary Examiner—Lionel M. Shapiro
Attorney, Agent, or Firm—Bernard, Rothwell & Brown

[57] ABSTRACT

A method is disclosed for producing L-phenylalanine using, as a catalyst, phenylalanine ammonia-lyase (PAL). Reducing agents are added to a bioreaction mixture containing t-cinnamic acid and ammonia or soluble ammonium salts, in order to reduce the effects of oxygen on catalyst life. The reducing agents of the invention include any substance that lowers the overall electrochemical potential of the solution, or which has a tendency to donate electrons to an oxidizing agent.

6 Claims, No Drawings

STABILIZATION OF PHENYLALANINE AMMONIA-LYASE IN A BIOREACTOR USING REDUCING AGENTS

BACKGROUND OF THE INVENTION

Enzymatic methods using L-phenylalanine ammonia-lyase for the conversion of trans-cinnamic acid to L-phenylalanine generally comprise the steps of (a) aerobically propagating a phenylalanine ammonia-lyase (hereinafter PAL)-producing microorganism in an aqueous nutrient medium until substantial amounts of PAL are produced, (b) contacting the cells of the PAL-producing microorganism from step (a), either as the whole culture broth or separated cells therefrom, or the isolated enzyme, with ammonium ions and transcinnamate ions and allowing the reaction to proceed under controlled temperature and pH conditions until the conversion to L-phenylalanine is substantially complete and (c) separating and recovering the L-phenylalanine from the reaction mixture.

The foregoing method is described, for example, in British Pat. No. 1,489,468 (Oct. 19, 1977). A drawback to the use of this process for commercial production has been the relative instability of PAL, and its inhibition by the substrate, t-cinnamic acid. To drive the reaction toward the production of L-phenylalanine and to counteract the effects of substrate inhibition, the abovementioned British patent describes a process which employs large masses of PAL-containing cells and excess concentrations of ammonium ions.

Yamada, S. et al. (*Appl. and Environ. Microbiol.*, 42, 7873–778 (1981)) have described the production of L-phenylalanine from t-cinnamic acid using PAL-containing *Rhodotorula glutinis* cells. They speculated that the lack of previous practical application of this process was attributable to the low activity and instability of microbial PAL. Yamada, et al. found that L-isoleucine had a stabilizing effect on PAL, and extended the useful period of activity of the enzyme. These authors further observed the inhibitive effect of the substrate, noting that at practical concentrations of t-cinnamic acid (150 mM), the rate of conversion of L-phenylalanine was reduced to one-half the maximum rate.

Despite the improvements described above, the instability and low activity of PAL has continued to be a disadvantage of this process. Accordingly, a need exists for procedures for stabilizing the enzyme and improving the PAL process for producing L-phenylalanine.

SUMMARY OF THE INVENTION

In accordance with the present invention, a method for significantly increasing the lifetime of the enzyme, phenylalanine ammonia-lyase, in a bioreaction mixture for producing L-phenylalanine, involves adding a chemical reducing agent or agents to the bioreaction mixture. A chemical reducing agent is defined, for the purposes of this invention, as any substance that lowers, i.e., makes more negative, the overall electrochemical potential of the mixture. Alternatively, the definition may include any substance that has a tendency to donate electrons to an oxidizing agent, i.e., a tendency to become oxidized.

DESCRIPTION OF THE INVENTION

In copending United States patent application Ser. No. 547,258, filed Oct. 31, 1983, it is disclosed that phenylalanine ammonia-lyase is sensitive to degradation in the presence of oxygen and under the influence of mechanical agitation. Accordingly, that patent application teaches that the stability and useful life of the enzyme can be improved if the bioconversion reaction is conducted under substantially anaerobic, static conditions.

In another copending U.S. patent application Ser. No. 547,139, filed Oct. 31, 1983, the fermentative process for producing PAL includes maintaining the fermentation medium under substantially anaerobic, static conditions following PAL induction. The exact mechanisms by which these conditions improve the stability of the enzyme are not well understood, but in addition to reducing the chemical and mechanical effects of oxygen and agitation, it is believed that these conditions also reduce the metabolic activities of the cells, with a concomitant decrease in the proteolytic breakdown of the enzyme.

In contrast to the above inventions, the present invention provides for reducing the effect of oxygen in a bioconversion reaction by adding to the mixture one or more reducing agents. The presence of the reducing agent or agents is advantageously maintained in the mixture during the entire reaction process.

A chemical reducing agent is defined, for purposes of this invention, as any substance that lowers, i.e., makes more negative the overall electrochemical potential of the bioreaction mixture. Alternatively, the definition may include any substance that has a tendency to donate electrons to an oxidizing agent, i.e., a tendency to become oxidized.

Preferred chemical substances useful as reducing agents of the invention include: hydrogen sulfide, thioglycolic acid, thiosulfuric acid, nitrous acid, sulfurous acid, ammonium and metal salts of the above, dithiothreitol, ethylmercaptan, ethylenemercaptan, methylmercaptan, 2-mercaptoethanol, hydrogen, nitrous oxide, iron (II) compounds, manganese (II) compounds, sulfur and zinc. Other reducing agents which are likely to be effective in stabilizing PAL may occur to those skilled in the art.

The PAL-producing microorganisms employed in the method of this invention require oxygen for growth; therefore, the cells are initially cultivated under aerobic, growth-promoting conditions. Generally, conventional procedures are employed for growing the cells. Cells are inoculated into a nutritional medium containing assimilable sources of carbon and nitrogen and essential vitamins, minerals and other growth factors. Suitable carbon sources can include various refined or crude carbohydrates such as glucose, sucrose, molasses, starches, grains and the like. A preferred carbon source is glucose. Nitrogen sources include inorganic ammonium salts, such as ammonium phosphate, ammonium sulfate, ammonium acetate, ammonium citrate, ammonium nitrate and the like and organic nitrogeneous substances such as soybean meal, meat infusions, amino acids, corn steep liquor, protein hydrolyzates, peptone, yeast extracts, and the like. A preferred nitrogen source for the process of this invention is yeast extract, and this nutrient may advantageously be combined with diammonium phosphate which supplies both nitrogen and phosphorous.

Vitamins, minerals and other growth factors may be supplied by the carbon and nitrogen sources (e.g., via the yeast extract) or may be supplied separately. These components can vary with the particular microorganism employed. Typically, trace minerals such as zinc, manganese, iron, cobalt, and calcium can be supplied in growth-promoting amounts as inorganic salts. These minerals may, for example, be supplied with process water, e.g., tap water, sea water, etc. Nutrient media of the type described are well-known, and can vary in composition widely.

After growing the cells to the desired cell density under aerobic conditions, they are induced to make PAL under aerobic, PAL-producing conditions. PAL induction is generally achieved by adding small amounts of a compound that acts as a substrate for the PAL. L-Phenylalanine is a good PAL inducer, and a number of analogs of L-phenylalanine also induce the synthesis of this enzyme. For example, D,L-phenylalanine, L-tyrosine, and D,L-tyrosine can be employed for this purpose. In addition, it has been discovered that various crude nitrogen sources can be used for PAL induction. Such crude nitrogen sources include hydrolyzed proteins which contain substantial amounts of L-phenylalanine or L-tyrosine. Casein and blood hydrolyzates can advantageously be used as crude nitrogen sources for the induction of PAL synthesis.

The PAL inducer is added to the cells in a PAL-inducing amount, which generally ranges from about 0.1 to 10 g/l of the fermentation medium. Preferably, the PAL inducer is employed at a concentration from about 4 to about 8 g/l of the fermentation medium. During this step, PAL-inducing conditions of temperature and pH, aeration and agitation are maintained. The temperature and pH are generally maintained within physiologically compatible limits during PAL induction. Somewhat reduced temperatures, e.g. from about 15° C. to about 25° C. are preferred, because at these lower temperatures, enzyme stability is improved and the rate of consumption of the PAL inducer is decreased. A preferred pH for the PAL induction ranges from about 5.5 to about 7.5, where relatively higher PAL levels are achieved.

If the cells employed are sensitive to catabolic repression of PAL synthesis, then, prior to induction, means should be employed to reduce or eliminate catabolites and their precursors from the medium. This may be accomplished by separating cells from the medium, washing them and suspending them in a catabolite-free medium. Alternatively, the cells can be allowed to grow until the nutrients are substantially exhausted before the PAL induction procedure is initiated.

The cells are advantageously cultivated under PAL-inducing conditions until the PAL activity reaches at least about 0.5 units per ml, preferably at least about 2.0 units per ml. A unit of PAL activity is defined as the amount of enzyme which catalyzes the formation of 0.83 mole of t-cinnamic acid per minute at 22° C. or 1 mole per minute at 30° C. It has been observed that under these conditions, the PAL activity increases to a certain point and then begins to diminish. PAL produced by these procedures may be employed to produce L-phenylalanine from t-cinnamic acid and ammonia. These reactants can be added directly to the PAL-containing cells in an aqueous medium, or the cells or enzyme isolated therefrom can be immobilized by known procedures on a solid support that can be reused for so long as the enzyme activity is maintained.

L-Phenylalanine is produced by this method under L-phenylalanine-producing conditions. These conditions will vary, depending upon the particular microbial strains employed, whether whole cells or cell-free enzyme preparations are used and whether immobilized systems are employed. In general, the reducing agent or agents are added to the bioreaction prior to or simultaneously with the addition of the t-cinnamic acid and ammonia.

The t-cinnamic acid and aqueous ammonia (or soluble ammonium salts) are supplied in amounts such that the ammonia is substantially in excess of the t-cinnamic acid on a molar basis. The t-cinnamic acid is employed in amounts of from about 5 to about 30 g/l, preferably from about 10 to about 20 g/l of the reaction mixture. At these t-cinnamic acid concentrations, the ammonia concentration generally ranges from about 0.1 to about 9.0 molar, preferably from about 4.0 to about 8.0 molar. The PAL-catalyzed reaction of t-cinnamic acid and ammonia to produce L-phenylalanine is reversible, and in fact, the equilibrium favors the breakdown of L-phenylalanine. Therefore, to establish a favorable reaction rate, the t-cinnamic acid concentration in the reaction mixture is advantageously maintained at a relatively high level. On the other hand, excessively high concentrations of t-cinnamic acid can inhibit the activity of PAL. Accordingly, a preferred procedure of this invention involves periodically or continuously feeding t-cinnamic acid into the reaction mixture during all but the latter stage of the reaction to maintain the concentration of this reactant within the ranges referred to above. Temperature during L-phenylalanine production is generally maintained within physiologically acceptable limits. The temperature preferably ranges from about 5° C. to about 40° C., most preferably from about 15° C. to about 25° C. These lower reaction temperatures have been found to prolong enzyme stability, without deleteriously affecting reaction rates. L-phenylalanine-producing conditions also include an alkaline pH, which generally can range from about 9 to about 11, preferably from about 10.4 to about 10.8.

Preferred ammonium salts are those which contain no halogen ions. The presence of halogens in the substrate solution has been found to inhibit the catalytic activity of PAL. Therefore, preferred ammonium salts include ammonium carbonate, ammonium sulfate, ammonium nitrate, ammonium citrate, ammonium acetate, and ammonium phosphate. An especially preferred ammonium salt is ammonium carbonate, which can be added in amounts ranging from about 50 to about 200 grams per liter. A convenient procedure for preparing a substrate solution is to dissolve the t-cinnamic acid in an aqueous ammonia solution, and then adjust the pH of the solution as desired by sparging with carbon dioxide or adding a mineral acid, such as sulfuric acid.

Generally, the reducing agent or agents are added in amounts of from about 1 to about 20 millimoles per liter. Preferably, they are added in amounts of from about 4 to about 10 millimoles/liter. In the case of chemical reducing agents which are gases, e.g., hydrogen or hydrogen sulfide, contact between the agent and the solution is made by blending the substance with an inert gas, e.g., nitrogen, in a suitable ratio (that is, from about 0.1% to about 10%) and filling the headspace of the bioreactor with the gas mixture under a pressure slightly greater than atmospheric. In the case of chemical reducing agents which are insoluble solids, e.g., sulfur or zinc, the substances are added to the solution in the form of a finely divided powder. Preferred reducing agents include 2-mercaptoethanol and thioglycolic acid.

The bioreaction is carried out until substantial amounts of L-phenylalanine have accumulated in the reaction mixture. Throughout the bioreaction, the concentration of reducing agent is advantageously maintained by periodic additions, if required. Generally, recovery procedures are initiated when the L-phenylalanine concentrations reach about 30 g/l, preferably about 45–50 g/l. L-Phenylalanine can be recovered from the reaction mixture by any suitable means. For example, solids can be removed by filtration or centrifugation to produce a clarified solution, and L-phenylalanine can be precipitated from that solution by adjusting the pH to the isoelectric point of L-phenylalanine, i.e., about 5.5

The following examples further illustrate the present invention, and demonstrate the beneficial effects of employing reducing agents in the bioreaction on the stability and useful life of the PAL enzyme. These examples are not to be construed as limiting the present invention.

EXAMPLE 1

Microbial cells containing a high level of activity of phenylalanine ammonia-lyase (PAL) were produced by aerobic fermentation. A 14 liter fermentor containing 10 liters of nutrient medium was inoculated with a seed culture of *Rhodotorula rubra*. The nutrient medium consisted of: soy peptone 2.7%; casein hydrolysate (Sheffield NZ-Amine) 1.35%; and corn steep liquor 0.18%. The fermentor contents were aerated and agitated, and the pH was maintained at 6.0 by periodic additions of ammonia water or sulfuric acid. During the fermentation, the PAL activity of the cells was monitored, and when the PAL activity reached a maximum (approximately 22 hours after inoculation), the fermentation was stopped by shutting off the aeration and agitation. The vessel was de-aerated by sparging with nitrogen gas. The microbial cells were separated from the fermentation broth by centrifugation, and stored at 4° C.

Four 14 liter vessels were each filled with 13 liters of a substrate solution containing: ammonia, 4 mole/liter; ammonium sulfate, 100 gram/liter; and trans-cinnamic acid, 10 gram/liter. The pH of the solution was 10.5, and the temperature was maintained at 35° C. The vessels were deaerated by sparging with nitrogen gas, and 2-mercaptoethanol was added to three of the vessels in amounts of 100, 500, and 1000 mg/liter.

PAL-containing microbial cells were then added to all four vessels in the amount of 1.35 gram (dry basis) per liter. The vessels were agitated for one minute every three hours. Supplemental trans-cinnamic acid was added to the vessels in the amount of 2.5 gram/liter at 3, 6, 9, and 12 hours after the addition of cells.

After 15 hours, the concentration of L-phenylalanine in the reaction mixture was measured, and the PAL activity of the cells was determined. The results, which are shown in Table I, indicate that the stability of PAL was enhanced by the reducing agent, with the result that a greater quantity of L-phenylanine was produced. The optimum concentration for 2-mercaptoethanol is between 100 and 1000 mg/liter.

EXAMPLE 2

Four 14 liter vessels were each filled with 13 liters of substrate solution. In two of the vessels, the substrate solution contained: ammonia, 5 mole/liter; ammonium carbonate, 120 gram/liter; and trans-cinnamic acid, 10 gram/liter. The other two vessels contained a substrate solution composed of: ammonia, 4.2 mole/liter; ammonium sulfate, 75 gram/liter; and trans-cinnamic acid, 10 gram/liter. The pH in all four vessels was 10.5, and the temperature was maintained at 35° C. All four vessels were de-aerated by sparging with nitrogen gas. Finally, one vessel of each pair had 600 mg/liter of 2-mercaptoethanol added.

The reaction was started by adding PAL-containing microbial cells to each of the four vessels in the amount of 1.7 gram (dry basis) per liter. (The microbial cells were produced by the method of Example 1.) The vessels were agitated for one minute every three hours. Supplemental trans-cinnamic acid was added to all four vessels in the amount of 2.5 gram/liter at 3, 6, 9, and 12 hours after the addition of cells.

After 15 hours, the concentration of L-phenylalanine in the reaction mixtures was measured, and the PAL activity of the cells was determined. The results are shown in Table II.

EXAMPLE 3

The optimum concentration of 2-mercaptoethanol was determined by carrying out reactions in five vessels with varying concentrations of 2-mercaptoethanol. The procedures used were the same as those described in Examples 1 and 2, with the following modifications. The nutrient medium for the fermentation was composed of: yeast extract (Amber Laboratories, Amberex 1003) 1.35%; corn steep liquor 0.18%; and L-phenylalanine 2.7%. The substrate solution for L-phenylalanine production contained: ammonia 5.1 mole/liter; ammonium sulfate 120 gram/liter; and cinnamic acid 10 gram/liter, with 2.5 gram/liter added at 3, 6, 9, and 12 hours after the addition of cells. The quantity of cells added to each of the vessels was 1.6 gram (dry basis) per liter.

After 24 hours, the L-phenylalanine concentration in the reaction mixture was measured, and the PAL activity of the cells was determined. The results are shown in Table III. The data indicate that the optimum concentration of 2-mercaptoethanol under these conditions is approximately 500 mg/liter.

EXAMPLE 4

PAL-containing microbial cells were cultivated in three 250-liter fermentors, each containing 163 liters of nutrient medium. The medium was composed of: yeast extract (Amber Laboratories, Amberex 1003) 1.38%; beet molasses 4%; diammonium phosphate 0.18%; and L-phenylalanine 0.92%. The fermentor was inoculated with a shake flask culture of *Rhodotorula rubra*. The fermentation was carried out at 30° C. with aeration and agitation. The pH was maintained at 6.0 by periodic additions of ammonia water or sulfuric acid.

During the fermentation, the PAL activity of the microbial cells was monitored, and when the PAL activity reached a maximum, at 28-30 hours after inoculation, the fermentations were stopped by shutting off the aeration and agitation. The vessels were de-aerated by sparging with nitrogen gas. Microbial cells were harvested by means of a Westfalia disc-bowl centrifuge. The combined yield of cells from all three fermentators was 5.04 kg (dry basis).

Substrate solution for L-phenylalanine production was prepared as follows. To a 300 gallon reactor vessel were added: trans-cinnamic acid 14 kg; ammonium carbonate 92 kg; and ammonia water (29%) 365 liters.

Water was added to bring the volume up to 900 liters. The contents of the vessel were agitated to dissolve the solids, and then deaerated by sparging with nitrogen gas. The pH of the solution was 10.5. Finally, 404 ml of 2-mercaptoethanol was added to serve as a reducing agent.

To start the reaction, the PAL-containing microbial cells were added to the reactor, in the form of a concentrated cell slurry. The contents of the reactor were then agitated briefly to disperse the cells. The temperature in the reactor was maintained at 30° C. The trans-cinnamic acid concentration in the reaction mixture was monitored at intervals of approximately two hours, and supplemental trans-cinnamic acid was added whenever necessary, to maintain a concentration of between 10 and 18 gram/liter. The amount of supplemental trans-cinnamic acid added during the reaction was 38.5 kg.

After 53.5 hours, the reaction mixture contained 33.3 gram/liter of L-phenylalanine and 18.6 gram/liter of trans-cinnamic acid. The total volume in the reactor was 1114 liters. The PAL activity of the cells in the reactor was 27% of the initial activity.

TABLE I

| Concentration of 2-mercaptoethanol | L-Phenylalanine Produced | PAL Activty (% of Initial) |
| --- | --- | --- |
| — | 5.71 gm/l | 22.8 |
| 100 mg/l | 7.34 | 31.2 |
| 500 | 9.26 | 39.4 |
| 1,000 | 8.54 | 35.9 |

TABLE II

| Type of Ammonium Salt | Concentration of 2-mercaptoethanol | L-Phenylalanine Produced | PAL Activity (% of Initial) |
| --- | --- | --- | --- |
| ammonium carbonate | — | 11.2 gm/l | 40.5 |
| ammonium carbonate | 600 mg/l | 12.9 | 46.6 |
| ammonium sulfate | — | 9.4 | 33.4 |
| ammonium sulfate | 600 | 10.8 | 38.7 |

TABLE III

| Concentration of 2-mercaptoethanol | L-Phenylalanine Produced | PAL Activity (% of Activity) |
| --- | --- | --- |
| 300 mg/l | 12.6 gram/l | 27.5 |
| 400 | 14.6 | 32.4 |
| 500 | 15.4 | 34.2 |
| 600 | 14.8 | 32.7 |
| 800 | 14.6 | 31.7 |

We claim:

1. A method for producing L-phenylalanine which comprises:
   (a) cultivating a PAL-producing microorganism under aerobic, growth-promoting conditions;
   (b) inducing the cells produced in step (a) to make PAL under PAL-producing conditions;
   (c) forming a bioreaction mixture by combining, under L-phenylalanine-producing conditions, the PAL produced by step (b) with t-cinnamic acid and ammonium ions in the presence of one or more reducing agents, to produce L-phenylalanine; and
   (d) recovering the L-phenylalanine so produced.

2. The method of claim 1, wherein the reducing agents are selected from the group consisting of: hydrogen sulfide, thioglycolic acid, thiosulfuric acid, nitrous acid, sulfurous acid, ammonium and metal salts of the above, dithiothreitol, ethylmercaptan, ethylenemercaptan, methylmercaptan, 2-mercaptoethanol, hydrogen, nitrous oxide, iron (II) compounds, manganese (II) compounds, sulfur and zinc.

3. The method of claim 2, wherein the reducing agent or agents are present in amounts of from about 1.0 to about 20 millimoles per liter of bioreaction solution.

4. The method of claim 3, wherein the bioreaction mixture contains initially from about 5.0 to 30.0 grams per liter of t-cinnamic acid, from about 0.1 to about 9.0 moles per liter of ammonia, and from about 50 to about 200 grams per liter of a soluble ammonium salt.

5. The method of claim 4, wherein the bioreaction is carried out at a pH of from about 9.0 to about 11.0 and at a temperature of from about 25° C. to about 40° C.

6. The method of claim 5, wherein the reducing agent is 2-mercaptoethanol or thioglycolic acid, and is in concentrations of from about 4 to about 10 millimoles per liter.

* * * * *